United States Patent
Chi et al.

(10) Patent No.: US 9,067,012 B2
(45) Date of Patent: Jun. 30, 2015

(54) RUGGED IV INFUSION DEVICE

(71) Applicants: Kevin Chi, Castro Valley, CA (US); Seth Robin Norman, San Francisco, CA (US); Matthew James Tilleard, New York, NY (US)

(72) Inventors: Kevin Chi, Castro Valley, CA (US); Seth Robin Norman, San Francisco, CA (US); Matthew James Tilleard, New York, NY (US)

(73) Assignee: CombatIV Inc., San Francisco, CA (US)

( * ) Notice: Subject to any disclaimer, the term of this patent is extended or adjusted under 35 U.S.C. 154(b) by 0 days.

(21) Appl. No.: 14/202,558

(22) Filed: Mar. 10, 2014

(65) Prior Publication Data

US 2014/0276427 A1    Sep. 18, 2014

Related U.S. Application Data (60) Provisional application No. 61/780,480, filed on Mar. 13, 2013.

(51) Int. Cl.
| | |
|---|---|
| *A61M 5/145* | (2006.01) |
| *A61M 5/155* | (2006.01) |
| *A61M 5/168* | (2006.01) |
| *A61M 5/142* | (2006.01) |

(52) U.S. Cl.
CPC .............. *A61M 5/145* (2013.01); *A61M 5/155* (2013.01); *A61M 5/16877* (2013.01); *A61M 2005/14264* (2013.01); *A61M 2005/14506* (2013.01)

(58) Field of Classification Search
CPC . A61M 5/145; A61M 5/155; A61M 5/16877; A61M 2005/14264
USPC ......... 604/131–134, 140–141, 147, 151, 153, 604/246, 257, 259, 262; 128/DIG. 12
See application file for complete search history.

(56) References Cited

U.S. PATENT DOCUMENTS

| | | | |
|---|---|---|---|
| 4,539,005 A * | 9/1985 | Greenblatt ............... 604/141 |
| 4,915,693 A | 4/1990 | Hessel | |
| 5,232,439 A * | 8/1993 | Campbell et al. ............ 604/28 |
| 5,370,622 A * | 12/1994 | Livingston et al. ......... 604/151 |
| 5,529,214 A | 6/1996 | Lasonde et al. | |
| 6,406,458 B1 * | 6/2002 | Tillander ................. 604/147 |
| 6,413,239 B1 | 7/2002 | Burns et al. | |
| 2006/0229558 A1 | 10/2006 | Heston et al. | |
| 2007/0135765 A1 * | 6/2007 | Miller et al. ............... 604/131 |

* cited by examiner

*Primary Examiner* — Theodore Stigell
*Assistant Examiner* — Amber Stiles
(74) *Attorney, Agent, or Firm* — Cozen O'Connor (57) ABSTRACT

A rugged infusion device capable of exerting consistent pressure onto an IV bag for intravenous medical use, wherein said device and said IV bag are surrounded by a rugged outer shell having a proximal and distal parts with respect to the device, said distal part comprising one or more of a flow regulator, a modulator, and a flow meter for regulating, smoothing, and measuring the flow of fluids effused from the IV bag, wherein said rugged proximal parts are capable of absorbing impacts to minimize the force imparted to the rugged infusion device.

10 Claims, 12 Drawing Sheets

RUGGED IV INFUSION DEVICE

BACKGROUND OF THE INVENTION

The present application is related generally to infusion pumps for the delivery of fluids to a patient. More particularly, embodiments of the invention disclose rugged, pre-filled mechanical or elastomeric pumps that are suitable for storage and transportation in a field bag and for immediate use on an injured patient, where the elastomeric or mechanical infusion pump expels fluids under pressure.

Typical IV fluid delivery devices rely on a bag of fluids, which is then infused with additional medications, whether it be to treat pain, administer antibiotics, or otherwise administer fluids or medication to a patient. These IV fluid bags require elevation for gravity feeding of fluids, typically through the use of an IV stand, or other feature to hold the IV bag at a proper elevation to provide consistent pressure for the delivery of these fluids. In a hospital setting, this is not a large issue as an IV stand can easily be situated near a patient's bed or an electronic infusion pump can be utilized. However, even in hospital environments, this IV stand then must be carted with a patient as the patient is moved. Furthermore, the IV stand is another apparatus that adds clutter to a hospital room.

Electronic infusion pumps may solve some of the issues related to gravity fed delivery of fluids. However, many circumstances are present where electronic infusion pumps are not practical or feasible. There is an unmet need for a rugged infusion pump suitable for use in circumstances where electronic infusion pumps are unavailable.

In situations where no IV stand is available, and where no electronic source is available for use of an electronic infusion pump, for instance in a combat zone, or away from a hospital setting, when a patient is wounded and requires IV fluids, another person is often required to hold and elevate the IV bag to allow for the delivery of fluids. Having a person hold the IV bag wastes the resources of that person and also creates an inconsistent pressure source, as the IV bag is likely to be constantly moving.

Conventional elastomeric pumps are fragile, complicated to use, and are designed for insertion by highly trained medical professionals. These devices are typically meant for the delivery of small amounts of pain medication and are installed during a surgical process. These pumps are also typically delicate and not designed for use during turbulent transportation or during strenuous movement by a patient. Furthermore, these devices are seldom pre-filled with sterile fluids for immediate use. Instead, elastomeric pumps in the prior art are typically filled right before use, and are not capable of prolonged storage under pressure.

Elastomeric pumps, for example Hessel, U.S. Pat. No. 4,915,693 provides an elastomeric bladder infusion pump for delivering a pharmaceutically active material. However, Hessel requires the elastomeric bladder to be filled with a volume of fluids and medications for immediate use and contains no pump housing.

Lasonde et al., U.S. Pat. No. 5,529,214 describes an elastomeric pump that contains a pump housing, but again requires that the bladder be filled on the spot. Further, Lasonde et al. requires the use of a mandrel to be inserted into the hosing and secured to the housing and the bladder.

Burns et al., U.S. Pat. No. 6,413,239, describe an improved infusion pump that, like Hessel and Lasonde, must be filled on the spot. Further, Burns et al. requires the use of an insertion member that stretches the elastomeric bladder in a radial, but not axial direction and a cap that seals one end of a balloon.

Heston et al, U.S. Pub. No. 2006/0229558, Oct. 12, 2006, describes an elastomeric infusion pump and an axially-variable core positioned within the bladder. Again the liquid is supplied by an external source at the point of infusion.

The prior art contains products that are inefficient, inaccurate, and possess inadequate pressure. IV bags are inefficient as they need to be elevated at a consistent height to provide for consistent and accurate delivery of fluids via gravity. In a location without an IV stand, typically another person would be required to hold an IV bag at a consistent height, which lacks the consistency and accuracy necessary for delivery of IV fluids and wastes human resources in combat situations.

IV bags are also consistently inefficient. They require manual regulation and measurement of flow. Fluid flow is typically measured by counting drops as they drip into a drip chamber from an IV bag. The flow rate can change based on the height of the bag. Regulating flow requires manual manipulation of a thumbwheel that is typical with IV bags, and requires recalibration when a patient moves, or when the height of the bag is changed.

Inaccuracies also plague IV bags. Any change in the position of the IV bag, movement by a patient, or change in venous pressure can drastically alter the flow rate of fluids from the IV bag to a patient. Accordingly, a trained medical advisor must frequently monitor IV bags to ensure that flow is within accepted ranges of the fluids being delivered.

Further, IV bags often lack adequate pressure for a fast flow rate or for I/O insertion. This requires a medical advisor or other person to manually squeeze an IV bag to provide sufficient pressure, again, wasting time and resources.

The prior art provides for elastomeric and or gravity devices that are to be filled on the spot by a medical practitioner and are not designed to store fluids under pressure for an extended period of time, and therefore are not suitable for immediate use within the field. Nor are these devices rugged enough for storage and use in medical field bags within military combat zones. Furthermore, these devices are typically used for very slow infusion, i.e. over the course of a number of days, utilizing low total volumes. Additionally, traditional drip IV devices are inefficient, inaccurate, and lack adequate pressure for many IV uses, especially outside of a medical facility. There is not a suitable solution for a rugged, pre-filled elastomeric or mechanical infusion pump capable of storing fluids under pressure for up to two years and suitable for being carried into the battle field and used on the spot without the need to fill the bladder, for delivery of fluids to a patient.

SUMMARY OF THE INVENTION

A rugged infusion pump suitable for containing sterile liquids under pressure and comprising a bladder capable of storing said sterile fluids and thereafter expelling said fluids under pressure and a device capable of providing a force on said bladder to expel fluids; further comprising a rugged outer shell comprised of a proximal and distal parts in relation to the bladder, said distal part comprising one or more of a flow regulator and a flow meter, and wherein said rugged proximal and distal parts are capable of absorbing impacts to minimize the force imparted to the infusion pump.

Another embodiment of the invention is a new and improved rugged infusion pump capable of storing and dispensing liquids under pressure and further comprising a bladder, a rugged outer shall, a flow regulator, a modulator, and a flow meter; wherein said bladder has a length, a width, and an opening at one end of said length; and wherein said bladder is capable of storing an amount of fluid under sustained pressure of about 20 PSI; rugged outer shell having a proximal and distal part in relation to the bladder, and a rugged inner housing having a proximal and distal part in relation to the bladder, comprising a shock absorbing material disposed there between, and wherein the proximal part comprises an outlet and inlet and said bladder being contained within the proximal part; said distal part comprising a flow regulator capable of limiting flow to about 0.1 to about 100 ml a minute, a modulator, and a flow meter.

Another embodiment of the invention provides for a rugged, pre-filled, rugged infusion pump comprising a sterile fluid suitable for infusion to a patient, and comprising a bladder capable of retaining sterile fluids under pressure, a rugged outer shell comprising a proximal and distal part in relation to the bladder, and a rugged inner shell comprising a shock absorbing material disposed there between the inner and outer layers, wherein the distal part surrounds one or more of a flow regulator, a modulator, and a flow meter; said proximal and distal parts capable of absorbing impacts to minimize the force imparted onto the infusion pump, and wherein said bladder, flow regulator, flow meter, and modulator are purged of air prior to storage of said fluids under pressure.

Another embodiment of the invention is a rugged pressure pump suitable for containing sterile liquids and comprising device to provide constant pressure to a traditional inert IV bag and thereafter expelling said fluids; further comprising a rugged outer shell comprised of a proximal and distal parts in relation to the bladder, said distal part comprising one or more of a flow regulator and a flow meter, and wherein said rugged proximal and distal parts are capable of absorbing impacts to minimize the force imparted to the infusion pump.

Another embodiment of the invention is a new and improved rugged IV infusion device comprising a device to provide constant pressure to a traditional inert IV bag, a rugged outer shall, a flow regulator, a modulator, and a flow meter; wherein said device is capable of provide a pressure of up to 20 PSI; said rugged outer shell having a proximal and distal part in relation to said inert IV bag, and a rugged inner housing having a proximal and distal part in relation to the inert IV bag, comprising a shock absorbing material disposed there between, and wherein the proximal part comprises an outlet and inlet and said IV bag being contained within the proximal part; said distal part comprising a flow regulator capable of limiting flow to about 0.1 to about 100 ml a minute, a modulator, and a flow meter.

Another embodiment of the invention provides for a rugged, pre-filled, rugged IV pump comprising an inert IV bag comprising sterile fluid suitable for infusion to a patient, and comprising a device capable of providing constant pressure on said inert IV bag, a rugged outer shell comprising a proximal and distal part in relation to the IV bag, and a rugged inner shell comprising a shock absorbing material disposed there between the inner and outer layers, wherein the distal part surrounds one or more of a flow regulator, a modulator, and a flow meter; said proximal and distal parts capable of absorbing impacts to minimize the force imparted onto the rugged IV pump, and wherein said IV bag, flow regulator, flow meter, and modulator are purged of air prior to storage of said fluids under pressure.

DETAILED DESCRIPTION OF THE PREFERRED EMBODIMENTS

The embodiments of the invention and the various features and advantages thereto are more fully explained with reference to the non-limiting embodiments and examples that are described and illustrated in the accompanying drawings and set forth in the following descriptions of those drawings. The figures in the accompanying drawings are not necessarily drawn to scale and the feature of one embodiment may be employed with the other embodiments as the skilled artisan recognizes, even if not explicitly stated herein. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

As used herein, the term "about" means within 10% of a defined number. For example "about 100 mm" includes lengths of 90 mm-to 110 mm.

Figure 1:
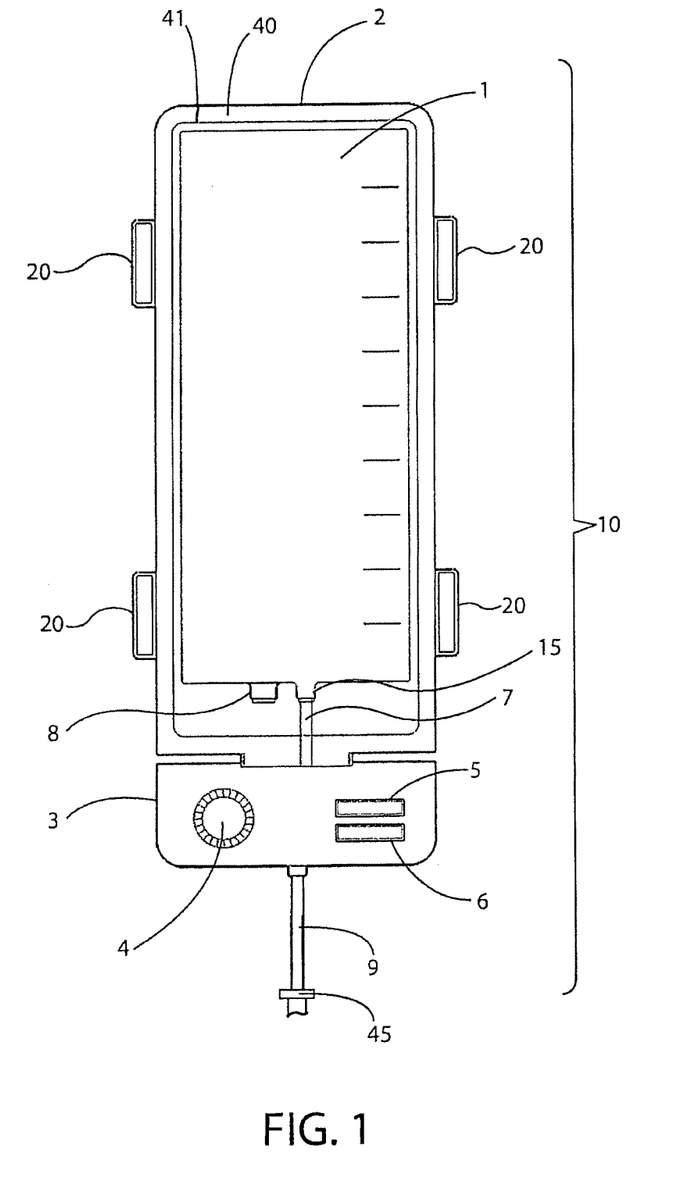
FIG. 1 is a perspective view of an rugged infusion device of one embodiment of the present invention.

Referring specifically to FIG. 1, what is drawn is an rugged infusion device 10. The rugged infusion device 10 includes an outer proximal housing 2, having a cylindrical shape, and being hollow, and a distal housing 3, which is cylindrical in shape and is hollow. The proximal housing 2 has a length, a diameter, a generally flat top and a generally flat base. The proximal housing 2 and distal housing 3 are typically made of a plastic material. The plastic material may be clear or opaque material, as necessary.

The proximal housing 2 and distal housing 3 are to be lightweight, but of sufficient strength to allow transport in a medical field bag, without concern for breakage. The proximal housing 2 is made of a sufficiently rigid material, often a clear plastic, capable of providing sufficient rigidity to prevent breakage of the housing, but also providing some absorptive properties, to lessen the impact on the bladder 1 and other components stored inside the proximal housing 2. Such materials are plastic and plastic polymer materials having a wall diameter of about 0.1 to about 5 mm, or about 0.5 to about 3 mm, or about 1 to about 2 mm in diameter.

The proximal 2 and distal 3 housing may be a single layer of such material. However, in other embodiments the proximal 2 and distal 3 housings may be an outer layer in addition to an inner proximal housing 41 and a corresponding inner distal housing, with a non rigid shock absorbing material 40 sandwiched between the proximal housing 2 and the inner proximal housing 41. Such shock absorbing material 40 may be any number of lightweight shock absorbing materials capable of being sandwiched between the inner and outer layers. Proximal housing 2 material and inner proximal housing 41 material may be the same or different materials. Accordingly, a rigid material may be used for the proximal housing 2 and a non-rigid material utilized for the inner proximal housing 41.

The proximal housing 2 and distal housing 3, are sufficiently rugged to withstand about 100 to about 300 G's of force, or about 200 G's of force. The properties of the materials used for the proximal housing, as well as the materials situated within the housing, are sufficiently rugged to be placed within a typical 40-50 pound medical field bag, and situated to forces of 200 G. Furthermore, the housing and components within the housing are suitable for storage in temperatures from about 0 degrees Fahrenheit to about 120 degrees Fahrenheit.

Other embodiments may utilize different materials for the proximal 2 and distal 3 housing, or the inner proximal housing 41, such as polyethylene terephthalate (PET), as is frequently used for plastic drinking bottles and other plastic and plastic polymer materials. Such materials provide a covering to reduce puncture of the bladder and provides some rigidity and support, but are also pliable enough to dissipate the impact of a direct force throughout the material, lessening the impact upon the bladder and other components. Furthermore, the materials may be colored or opaque as is necessary for camouflage or for storage of medications within the rugged infusion device 10 that break down under light sources. The proximal housing 2 and distal housing 3 may be made of different materials.

The purpose of the proximal housing 2 is to protect the bladder 1 and other contents situated within the proximal housing 2 from breakage. Typically, the material for the proximal housing 2 requires a thickness of about 0.01 to about 5 mm, and more particularly from about 0.1 to about 1 mm thickness.

The proximal housing 2 and distal housing 3 are not intended to be air tight. Accordingly, changes in air pressure, typically encountered via helicopter and other military air transport, will not impact the integrity of the proximal housing 2 or distal housing 3.

Attached to the proximal housing 2 are strap holes 20. The strap holes 20 are placed two on each side of the lengthwise portion of the housing, and paired so that a corresponding strap hole 20 is on an opposing radial side. Each pair should align with another pair to allow for use of straps and attachment to a body.

The distal housing 3 contains a regulator dial 4, a flow rate display 5, and a volume infused display 6, as well as the regulator, flow rate mechanism and volume mechanism within the distal housing 3. Typically, the material for the distal housing 3 requires a thickness of about 0.01 to about 5 mm, and more particularly from about 0.1 mm to about 1 mm thickness. The distal housing 3 is made of a plastic, resin based, or metallic material. The material may be transparent, translucent or opaque. The distal housing 3 may be made of the same or similar material as the proximal housing 2, so as to protect the instruments situated inside the distal housing 3.

Within the distal housing 3 are situated mechanisms for regulation of flow, calculating flow rate, calculating volume infused, smoothing pressure and regulating pressure, among other features. The distal housing 3 may comprise all of these features, some of these features, or combinations of these features. Some features may also be situated within the proximal housing 2, or may be situated such that some part of a feature is located in both the proximal housing 2 and distal housing 3.

The proximal housing 2 and distal housing 3 refer to the proximity of each housing to the bladder 1. The proximal housing 2 surrounds the bladder 1, whereas the distal housing 3 surrounds and protects additional features of the invention. As seen in the figures herein, the distal housing 3 is depicted at either end of the proximal housing 2. However, the point of attachment of the proximal and distal housings may be at other points in relation to the proximal housing 2.

Situated within the proximal housing 2 is a bladder 1. The bladder 1 is made of an inert material, such as rubber, plastic, silicon or other suitable material that can be filled with a volume of fluids to be given by IV to a patient. The bladder 1 has a length and a width, and is capable of being filled and stored under pressure. The elastomeric bladder 1 is a sufficiently rugged material, having a thickness of about 0.01 to about 5 mm, or about 0.1 to about 3 mm, or about 1 mm to about 2 mm in thickness. Accordingly, the material is intended to withstand impacts of up to 300 G's.

The shape of the bladder 1 is approximately rectangular or slightly cylindrical in shape, and is generally longer than the width or diameter. In some embodiments, the length of the bladder is about 2× the width to about 20× the width, about 2× the width to about 10× the width, and about 3× the width to about 5× the width.

Figure 5:
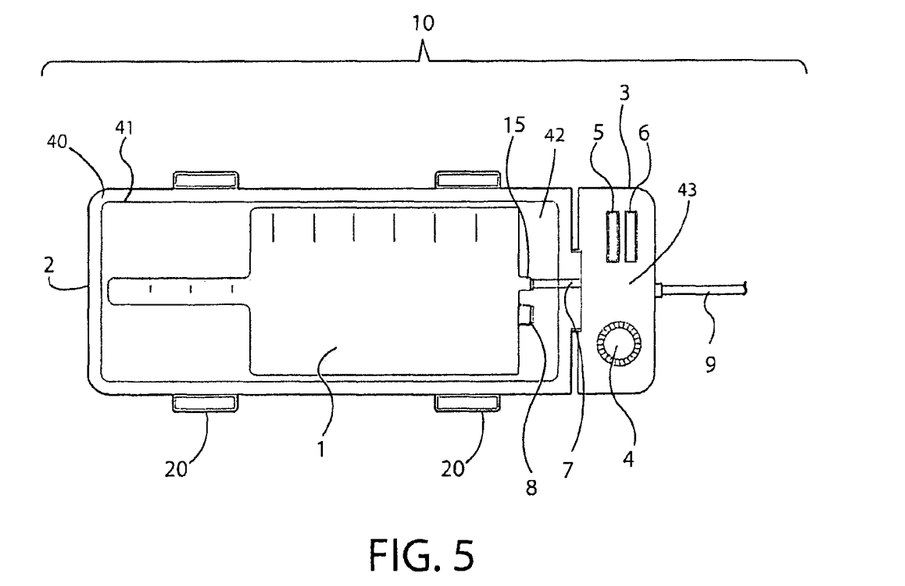
FIG. 5 is a perspective view of one embodiment of the invention described herein.
Figure 6:
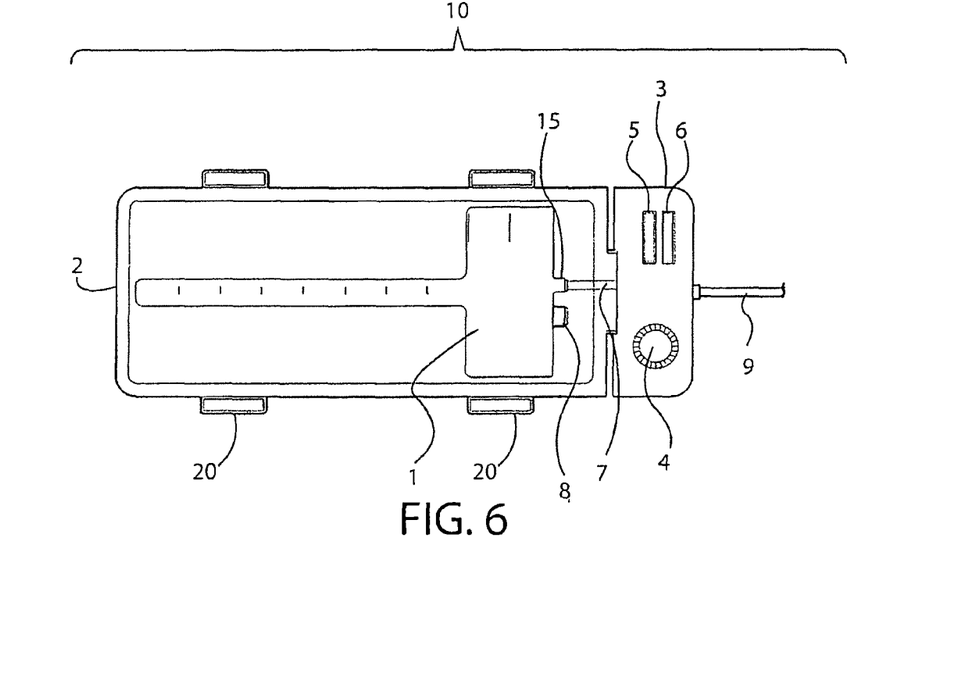
FIG. 6 is a perspective view of one embodiment of the invention described herein.

In cases where the bladder is elastomeric in nature, when the fluids are expelled, the bladder 1 will deflate and leave a portion of the bladder 1 as a "tail" as can be seen in FIGS. 5 and 6. The bladder 1 is capable of expelling about 95% of fluids stored within the elastomeric bladder at a consistent pressure. Other embodiments allow expulsion of about 99% to about 99.9% of fluids from the bladder 1 at a consistent pressure.

The bladder has at least one opening at one end of the lengthwise portion of the bladder. The bladder 1 is of such a volume that when full, fills about 75 percent to about 99 percent of the interior volume of the proximal housing 2. Alternatively, the bladder 1 fills about 75 percent to about 99 percent of the volume inside the inner proximal housing 41. The desirable property of the bladder 1 is the nature of its construction that it is sufficiently rugged for use as a field device.

The bladder 1 is capable of storing sterile fluids at pressure for an extended period of time, without rupture, while expelling fluids at a consistent pressure. The bladder 1 is able to be filled and used, up to two years after being filled. However, other embodiments have a shelf life of up to one year, up to six months, up to three months, up to two months, up to one month, up to 15 days, up to 7 days, and up to 1 day.

Alternatively, an embodiment utilizes a first inner bladder, such as a traditional inert IV bag, and is constructed such that the first bladder is situated within an elastomeric bladder. Thus, fluids would only be in contact with the first bladder, but, pressure would be provided by the elastomeric bladder situated outside of the first bladder.

An additional embodiment of the bladder 1 comprises an inert IV bag and contains strips of elastic materials surrounding the inert IV bag. This allows the strips of elastic materials to provide the necessary pressure on the inert IV bag for expulsion of fluids.

The rugged infusion device 10 further comprises bladder tubing 7 and a bladder clamp 15. The bladder tubing is made of an inert material, typically rigid plastic tubing. However, in certain circumstances, other materials may also be sufficient or necessary. The bladder tubing 7 typically has an inner diameter of 0.1 mm to about 5 mm, or about 1 mm. The bladder tubing 7 typically has a wall diameter of about 0.01 mm to about 2 mm, or about 1 mm. The bladder tubing 7 typically has an outer diameter of about 0.2 mm to about 7 mm, or about 1 mm to about 5 mm, or about 2 mm. The bladder tubing 7 connects the opening of the elastomeric bladder 1 to the features in the distal housing 3. Typically, the bladder tubing 7 will be connected to a flow regulator 14 (see FIG. 7) that is capable of holding liquids within the elastomeric bladder 1 for an undefined amount of time. The bladder tubing must be sufficiently rigid to allow the opening of the elastomeric bladder to be secured to the bladder tubing 7.

Figure 12:
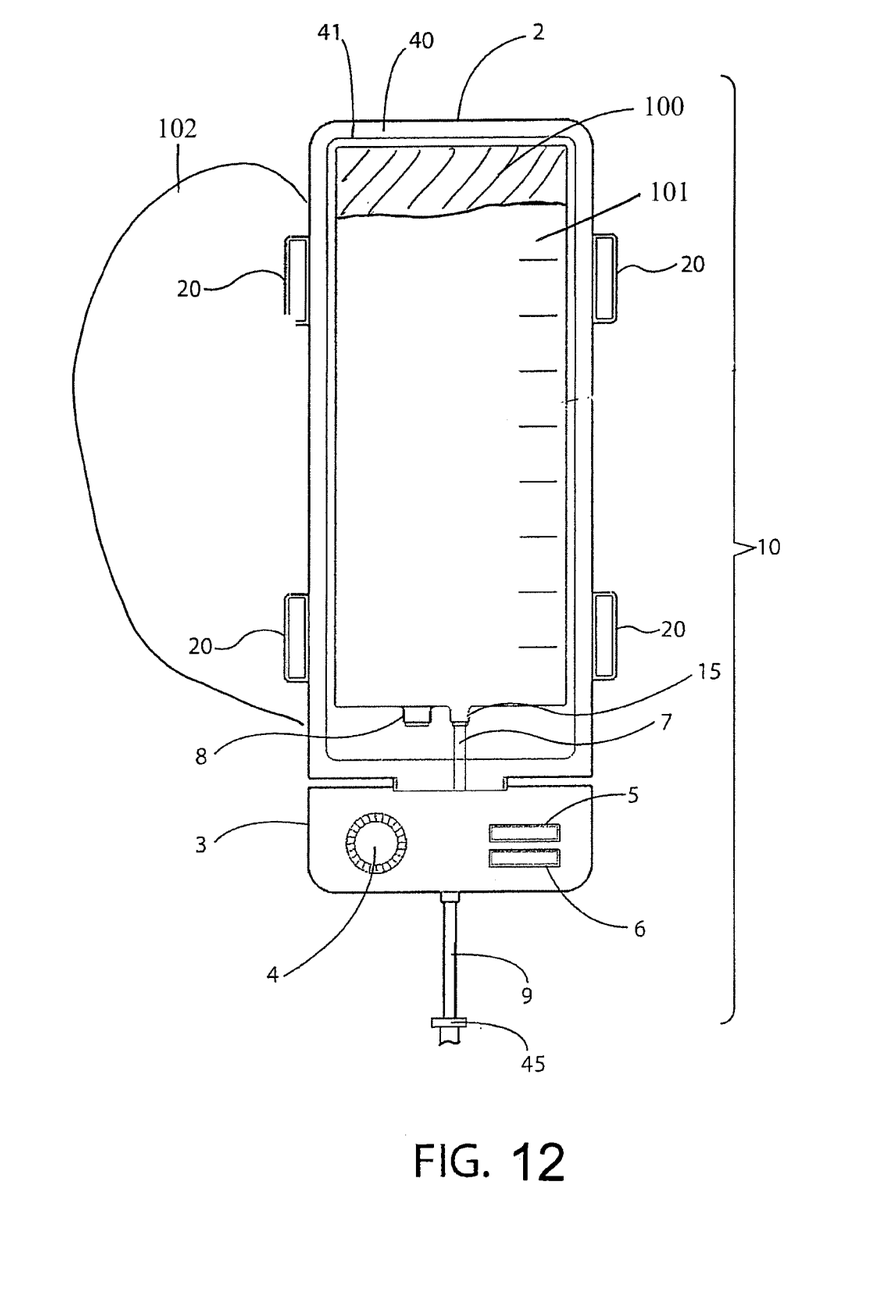
FIG. 12 is a perspective view of one embodiment of the invention described herein.

Other embodiments of the invention eschew an elastomeric bladder for an alternative pressure device 100 (See FIG. 12) to provide pressure onto a bladder that does not have the ability to self-expel fluids. A pressure source may include a spring or other mechanical device, or an electronic compression device that may provide pressure to an IV bag 101 situated within the body of the rugged device. This provides for the use of a traditional IV bag 101 and fluids stored or added thereto, and an external device to apply appropriate and sufficient pressure to the bag to eliminate the common issues with a traditional IV bag.

Figure 13:
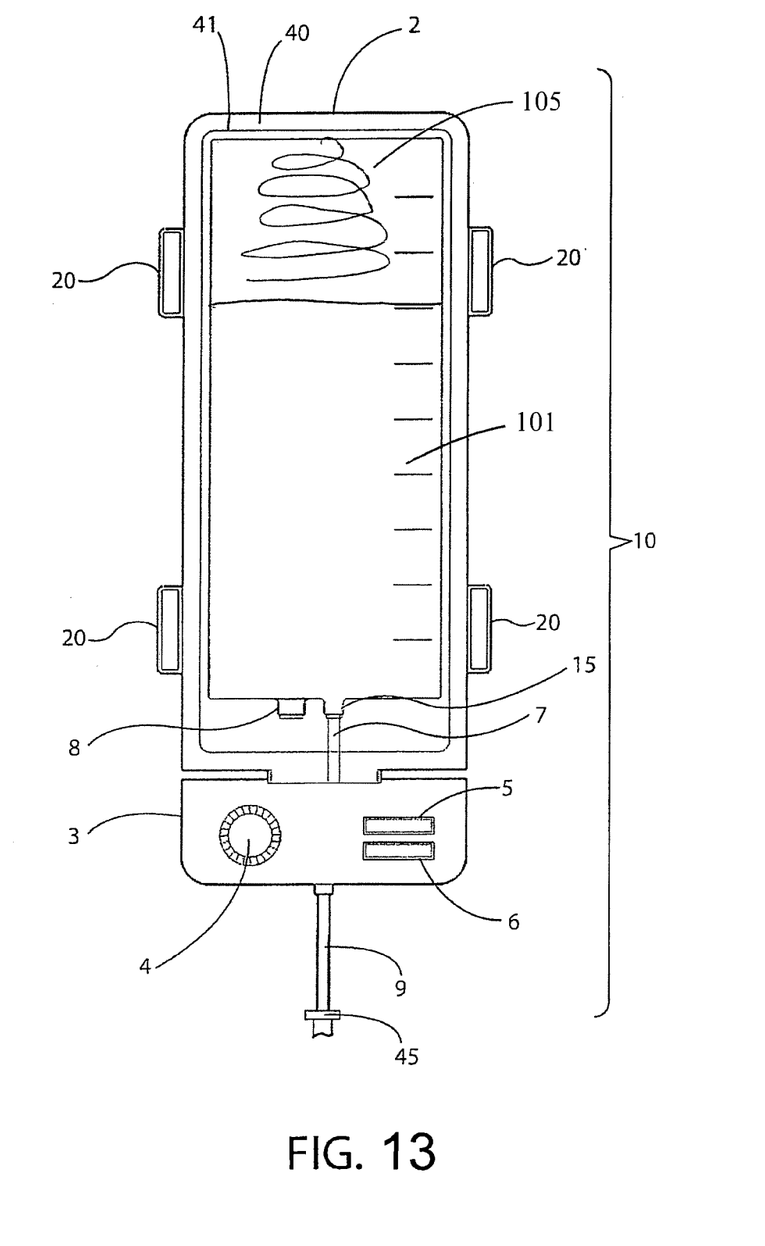
FIG. 13 is a perspective view of one embodiment of the invention described herein.

One such embodiment utilizes a spring 105 held in compression. When said spring is released by a trigger mechanism, the spring expands and thereby exerts a nearly constant force onto the IV bag 101 (See FIG. 13). The pressure on the IV bag 101 pushes fluid into the regulator mechanism and expels fluids at the appropriate pressure and volume according to the invention described herein.

Other suitable mechanisms including screw type mechanisms, level type mechanisms, or other means suitable for imparting a consistent force upon the IV bag or bladder. These may be wholly mechanical mechanisms, such as the spring, they may include a winding device to impart force, or be pre-loaded and released when use is required. Furthermore, simple electronic motors may be installed within said rugged infusion device that drives or presses upon the IV bag or bladder. Other such means as is known in the art is further suitable for imparting this consistent force.

Figure 15:
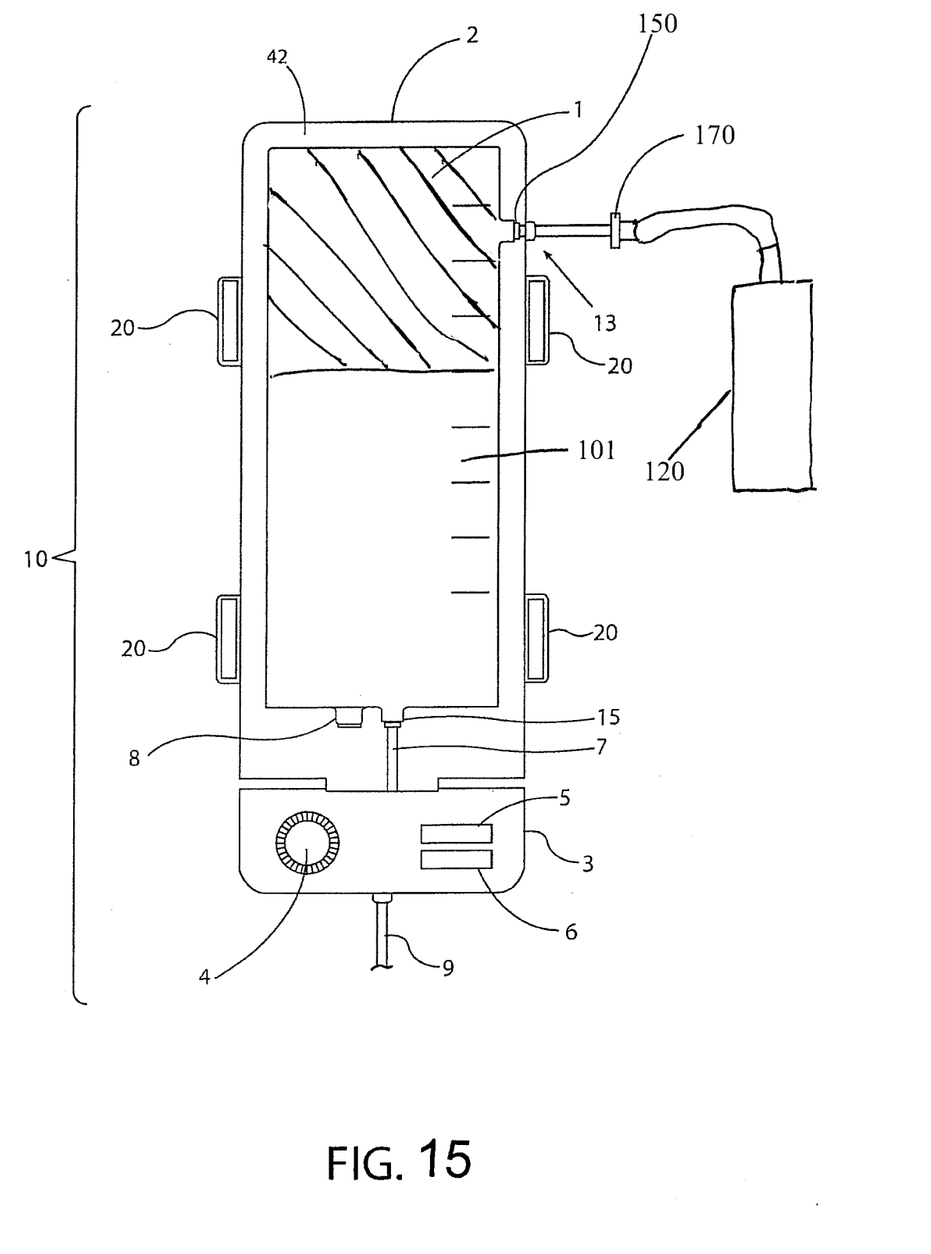
FIG. 15 is a perspective view of one embodiment of the invention described herein.

Another such mechanism for providing pressure includes a compressed gas canister 120 and a traditional inert IV bag 101 within the protecting casing (See FIG. 15). In this embodiment, the protective casing is airtight, allowing for the gas to provide pressure onto the IV bag 101. An attachment point to the casing at 150 provides air, and a point at 170 connects the canister 120 to the tubing to the casing. When triggered, the canister 120 releases gas at a constant rate providing increased pressure in the casing and thereby expelling fluids. Simple $CO_2$ canisters or other compressed air canisters are suitable for use in these scenarios.

Figure 14:
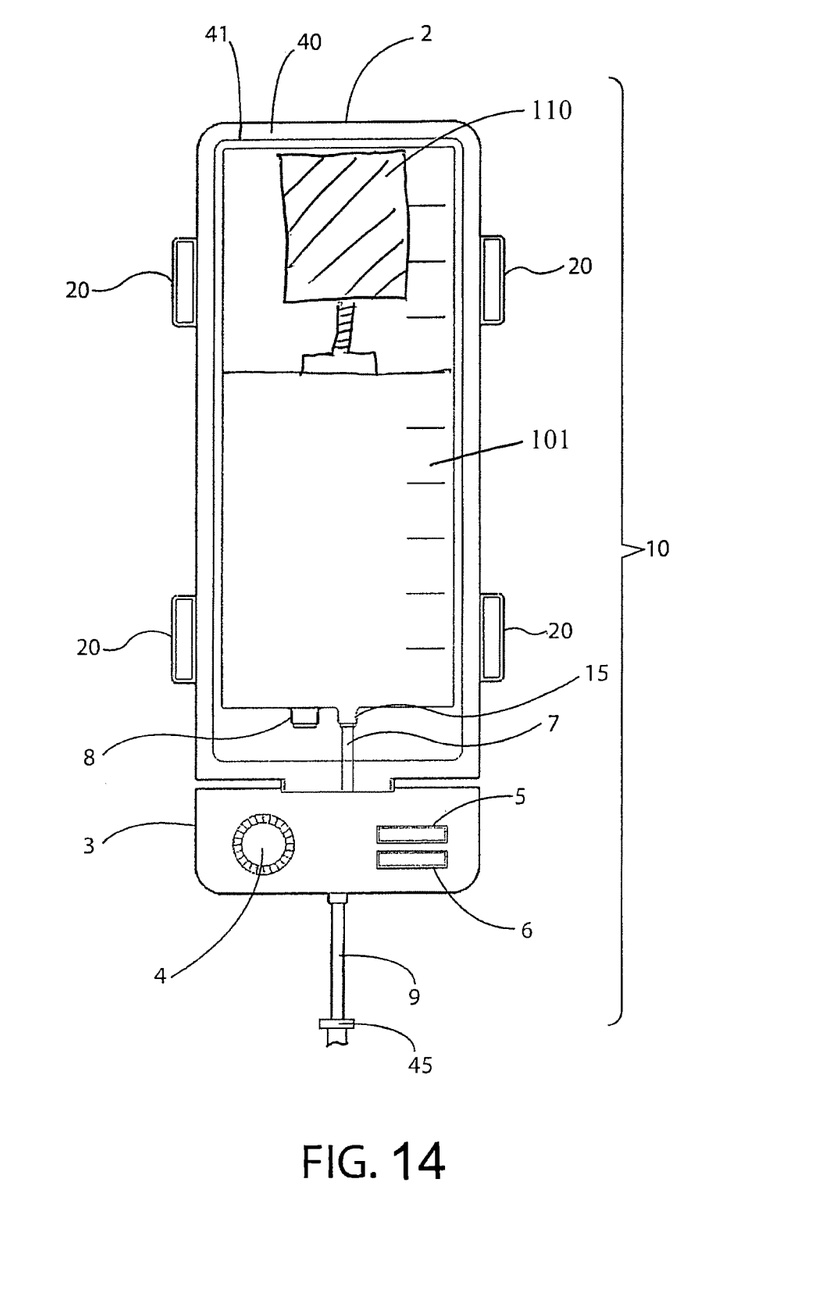
FIG. 14 is a perspective view of one embodiment of the invention described herein.

Similarly, the use of a mechanical device 110 or electronic device to provide pressure or to create air pressure can be utilized in connection with the embodiment (See FIG. 14). The device is capable of use in rugged environments and is capable of providing a consistent pressure to aid in the expulsion of fluids from and IV bag.

The bladder clamp 15, secures the opening at the one end of the longitudinal length to the bladder tubing. The bladder clamp 15 is one of any numerous small diameter lightweight clamps capable of securing an inert bladder to tubing.

The lower valve 8 allows filling of the bladder. This valve is also secured to the bladder 1 with a bladder clamp 15 similar in nature to the one used to secure the bladder 1 to the bladder tubing, however, the clamping device and valve may be a single piece. The valve allows filling of the bladder and then closing of the valve to secure the fluids within the bladder.

The rugged infusion device is intended to be stored full of fluids, such that the fluids are available for immediate use of the rugged infusion device 10. Accordingly, unlike typical IV bags, no air is present in IV bag or bladder of the device. Further, no air is provided within any of the tubing or features within the distal housing 3. Accordingly, the rugged infusion device 10 can be directly attached to an IV line and requires no drip line to eliminate air from the IV line. The bladder 1 may be of various volumes when expanded. Total fluids within an the bladder 1, are typically 250, 500, 750, 1000, 2000, 2500, and 5000 ml. The bladder 1 and housings 2 and/or 41 for each of these volumes will have a greater or smaller capacity, as necessary to store the liquid and allow for it to be expelled with the appropriate pressure.

The fluids within the rugged infusion device 10 are intended to be sterile fluids utilized with standard IV materials, such as a catheter inserted into a peripheral vein, typically in the form of cannula-over-needle type device. This allows for a secure connection of a catheter into a peripheral vein and allows for infusion of fluids from the rugged infusion device 10. Fluids may also be used with intraosseous insertion (I/O insertion), where appropriate. Other forms of delivery of fluids under pressure are also appropriate based on the needs of a particular patient.

The fluids within the bladder 1 are intended to be expelled with consistent pressure, within about 20%, or within about 10%, or within about 5%, or within about 1% of the initial pressure intended for use by a medical technician. This consistent pressure allows a medical technician to set a pressure and a flow rate and have minimal change in the flow rate based on changes in conditions of the patient, or more typically, changes in the elevation of an IV bag or pressure exerted on an IV bag by a person squeezing the bag.

The distal housing 3 is attached to the proximal housing 2 via any number of connection mechanisms. The distal housing 3 and proximal housing 2 may be welded together, chemically fused, glued, or mechanically attached to each other. The distal housing 3 and proximal housing may be connected at the outer edge of each part, or secured through other means, so long as space is provided to allow the bladder tubing 7 to run from the proximal housing 2 into the distal housing 3.

Contained within the distal housing 3 are certain features of the rugged infusion device 10 that facilitate and control the flow and measurement of fluids from the bladder 1 into a patient. The regulator dial 4 controls the flow out of the bladder 1. The regulator dial 4 is utilized in connection with a flow regulator 14 (see FIG. 7) to control the volume of fluids. The regulator dial may mechanically or electronically control the flow regulator 14 (see FIG. 7).

Also contained in the distal housing 3 is a flow rate display 5. The flow rate display 5 is a mechanical or electronic display showing the flow rate of fluids being expelled from the bladder 1. In contrast to the prior art, where drops of fluid are counted to determine flow rate, the flow rate display 5, displays the rate of flow of fluids, based on the use of a flow meter 11 (See FIG. 7).

Also contained in the distal housing 3 is a volume infused display 6 that provides a total measurement of the volume of fluids expelled by the bladder 1. This allows for quick reference as to the total volume a patient has received and for accurate display and calculation of fluids remaining, thereby aiding personal in treating and monitoring patients.

Finally, exiting the distal housing 3 is external tubing 9. This external tubing 9 allows for quick connection of the rugged infusion device 10 to commercially available IV and catheter lines, as necessary for infusion of fluids. In particular embodiments, the external tubing 9, may be pre-filled with saline solution, to ensure no air bubbles exist in the line. Further, the external tubing 9, ends with a drip lock 45, as found on standard IV drip bags, and allows for the external tubing 9 to be connected into a standard military issue IV port. Where the external tubing 9 is pre-filled with saline solution, all other lines within the rugged infusion device 10, are also pre-filled to prevent the introduction of air into the line.

To increase the ruggedness of the rugged infusion device 10, additional protective casings may be added to support connectors and or features within the proximal housing 2 and distal housing 3. The protective casings may be of the same or similar material as the rugged outer shell, or may include foam or rubber support where appropriate.

Similarly, the addition of a handle 102 (FIG. 12) or carrying device situated on the body of the protective casing may facilitate the ease of use and carrying of the rugged infusion device 10 and one or more embodiments utilizing a mechanical, air pressure, or other source to expel fluids from an IV bag under pressure.

Figure 2:
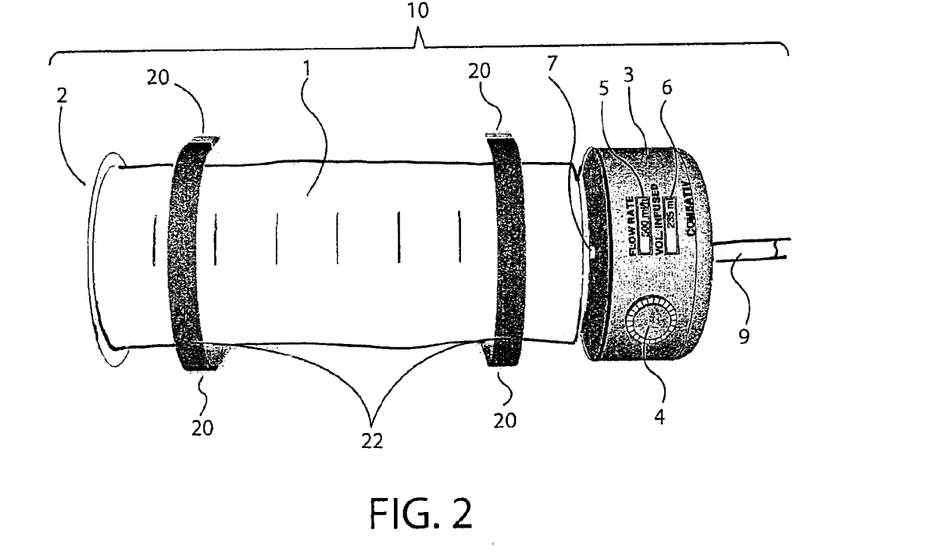
FIG. 2 is a perspective view of one embodiment of the invention described herein.

FIG. 2 displays a further embodiment of the rugged infusion device 10. In addition to the features described in FIG. 1, FIG. 2 displays an embodiment utilizing straps 22 over the proximal housing 2. The straps 22 attach around the proximal housing 2 to allow secure connection to a patient, or to another feature. Accordingly, the straps 22 provide a secure way to attach the rugged infusion device 10 to a patient, for example, to an arm or leg, allowing the rugged infusion device 10 to be secured to a patient without the need for external devices.

FIG. 2 further displays an embodiment of the invention described herein, where the proximal housing 2 is constructed of a transparent or semi-transparent materials, allowing a view of the bladder 1, whereas the distal housing 3 is shown with an opaque material so that the features within the distal housing 3 are not visible.

Figure 3:
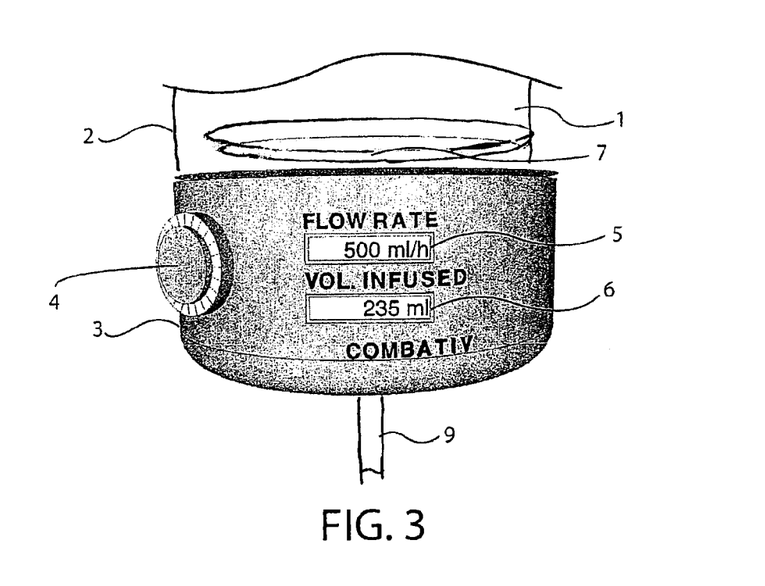
FIG. 3 is a perspective view of features of one embodiment of the invention described herein.

FIG. 3 is a detailed view of the distal housing 3, and external features thereto. In particular, the features of the regulator dial 4, the flow rate display 5, and the volume infused display 6, are prominently shown on the exterior surface of the distal housing 3. Further, the proximal housing 2 and the distal housing 3 may have the same diameter, and, for example, can be secured at the exterior edge of each of the parts, when secured above or below one another.

Figure 4:
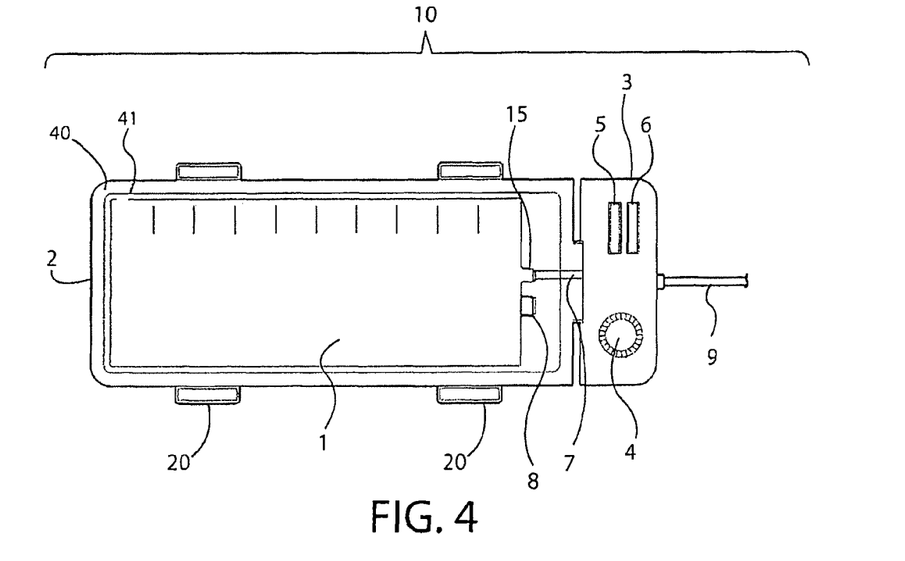
FIG. 4 is a perspective view of one embodiment of the invention described herein.

FIG. 4 identifies an embodiment of the rugged infusion device 10 where the bladder 1 is full. When full, the bladder 1 fills the space within the proximal housing 2. As intended, the bladder is filled lengthwise and laterally, to fill the space within the proximal housing 2. When full, the sterile fluids within the bladder 1 are stored under pressure. Additionally, FIG. 4 identifies a shock absorbing material 40, situated between the proximal housing 2 and in the inner proximal housing 41.

FIG. 5 is a representative example of an embodiment of the invention where the bladder 1 is in a partially deflated state. Accordingly, about ⅓ of the fluids have been expelled from the bladder 1. As can be seen, the bladder expels fluids but leaves a "tail" or empty portion of the bladder end of the bladder 1.

FIG. 5 further identifies a shock absorbing material 40, situated between the proximal housing 2 and the inner proximal housing 41. Such a shock absorbing material 40 and inner proximal housing 2 may have corresponding parts in the distal housing 3 (not shown). Furthermore, a foam core 41 is further situated inside the inner proximal housing 41, so as to provide an additional layer of support for the bladder 1. Additional the distal foam core 43, may support the features within the distal hosing, as necessary.

FIG. 6, like FIG. 5, depicts a representative embodiment of the invention, where the bladder 1 is about ⅓ full of fluids. FIG. 6 identifies the shape of the bladder as it deflates. Other embodiments of the bladder 1 may utilize an elastomeric design that aids in expelling fluids from the bladder, as depicted in FIGS. 5 and 6.

Figure 7:
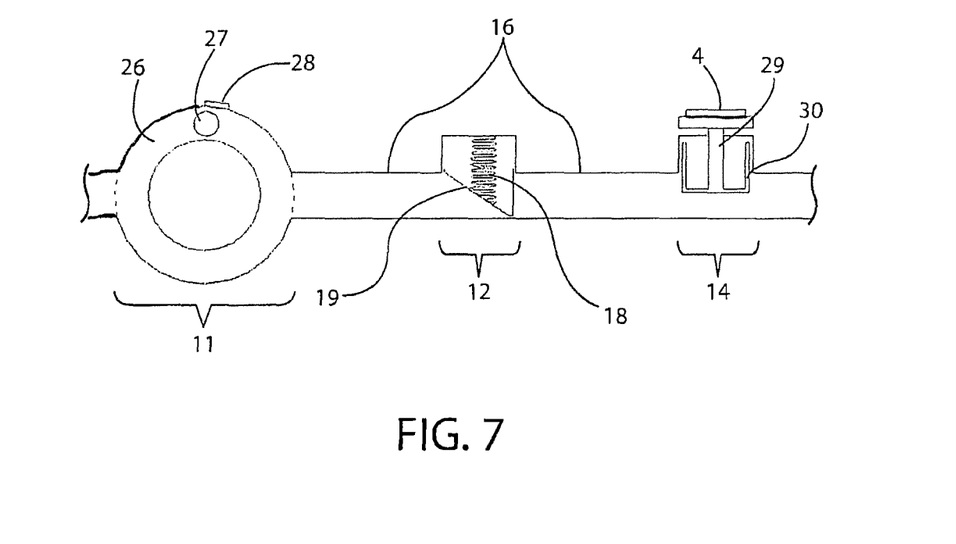
FIG. 7 is a perspective view of one embodiment of the invention described herein.

FIG. 7 identifies features of the invention that are intended to be situated within the distal housing 3. The flow meter 11 is a measuring device to calculate the rate of flow from the bladder 1. This allows for display of the flow rate on the flow rate display 5, and display of the volume of fluid infused, on the volume infused display 6. The flow meter 11 may be any type of volume and flow measurement devices as is known in the art. The flow meter as shown in FIG. 7 is a simple mechanical meter, that pushes fluids through the flow meter 11, which moves a revolving flow counter within a flow tube 26, each revolution marked by the flow notch 28. This allows a known volume of fluids to be mechanically marked. Fluids press against the flow mechanism 27, which revolves and by use of the flow notch 28, counts the flow of fluids through the flow meter 11. The flow notch 28, may be magnetic, or electronic, or of other material to mark each revolution.

Other forms of acceptable flow meters 11 include a rotating valve (shown in FIG. 7), nutating disc, piston meter (either oscillating or single piston), oval gear, rotating lobe, or rotating impeller types of flow meters. These are but a few examples of acceptable volumetric flow meters. What is required is simply a flow meter capable of measuring and recording volumes of fluid from about 0.01 ml to about 5,000 ml of fluid.

FIG. 7 further shows a modulator 12 that regulates the pressure within a fluid stream. The simple modulator 12 as shown in FIG. 7 is a spring activated modulator that modifies the opening size within a tube. FIG. 7 depicts the modulator 12 in line on the housing base connector tubing 16 where a modulator spring 18 regulates the opening within the modulator 12 and manipulates the modulator wedge to increase or decrease the opening within the modulator 12. The modulator smooths small changes in pressure from the bladder by adjusting the modulator wedge 19 to keep the volume of fluids being expelled consistent. This embodiment utilizes pressure imputed upon the modulator wedge 19, which engages the modulator spring 18, opening or closing the modulator 12 to compensate for changes in pressure. This is but one modulator mechanism that a person of ordinary skill in the art will recognize as suitable for use with the invention described herein.

Finally, FIG. 7 also shows a flow regulator 14. The flow regulator 14 is used in conjunction with the regulator dial 4 (see FIG. 1), to control the flow of fluids from the bladder. The flow regulator 14, as shown in FIG. 7 is one of any number of possible styles of regulators. The embodiment depicts a flow regulator 14 that utilizes a regulator body 30, which partially blocks the opening through the flow regulator 14 thus restricting the flow of fluids. The flow regulator 14 utilizes a regulator piston 29 to raise and lower the regulator body 30, and a regulator dial 4, that controls the regulator piston 29 position. This is one of a typical type of "gate valve" type flow regulator 14. Other types of flow regulators 14 are also acceptable, such as ball valves, needle valves, or other suitable valves to control the flow of fluids under pressure.

The flow regulator 14 is suitable for regulating the pressure of fluids from about 5 PSI to about 50 PSI. Other embodiments utilize a pressure of about 5 PSI to about 25 PSI, from about 10 PSI to about 20 PSI, and about 15 PSI, or about 20 PSI. Further, the regulator is able to limit flow from about 0.01 ml per minute to about 2500 ml per minute, from about 0.1 ml per minute to about 1000 ml per minute, from about 0.1 ml per minute to about 500 ml per minute, from about 0.1 ml per minute to about 250 ml per minute, from about 0.1 ml per minute to about 100 ml per minute, from about 0.1 ml per minute to about 50 ml per minute, and from about 1 ml per minute to about 10 ml per minute.

Figure 8:
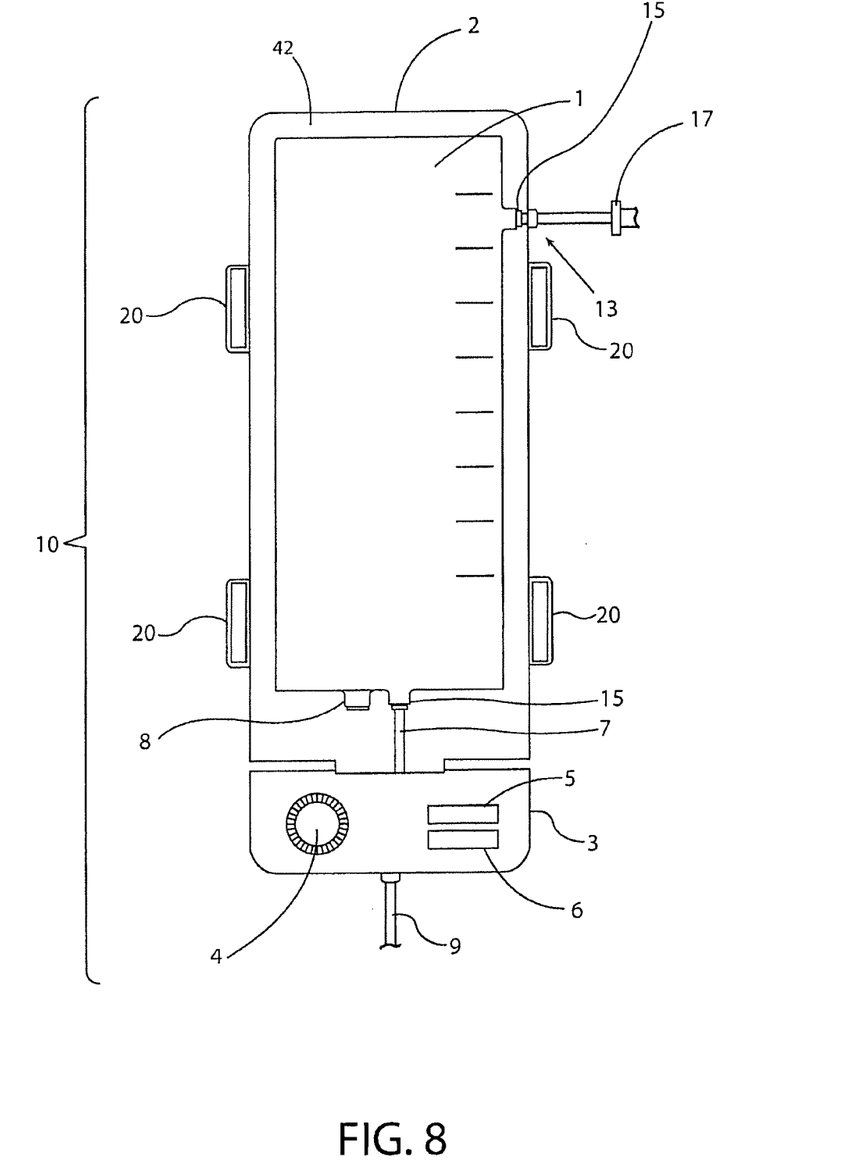
FIG. 8 is a perspective view of one embodiment of the invention described herein.

FIG. 8 depicts an embodiment of the invention described herein, that further incorporates an insertion port 17, for the addition of additional medications to the bladder 1. The insertion port 17 is connected to the bladder via an insertion tube 13, which is secured to the bladder 1, with a bladder clamp 15. The insertion port 17 allows for addition of medications to the pre-filled rugged infusion device 10. Certain instances may call for the use of any number of medications that are suitable or necessary for a patient.

Additional embodiments to create a rugged infusion device include the use of a rugged proximal housing 2 and distal housing 3 and comprising a foam core 42 within said outer proximal and distal housings 2 and 3. Said proximal and distal housings 2 and 3 capable of providing protecting from low impact forces, and said inner foam core protecting the rugged infusion device under greater forces, such as up to 300 G's or more. Said foam 42 may be molded to fit the shape of the hosing, or to accommodate instruments located within said housings. Additionally, said foam 42 may be injected into said housing once the bladder is full, to provide direct support for each individual feature. Said foam 42 may be rigid or soft and flexible foam, but of sufficient density to provide support and protection for the features within in the proximal and distal housings 2 and 3. The foam core 42 may be present solely in the proximal housing 2 or in the distal housing 3, or both.

FIG. 8 depicts the use of an insertion tube 13 that connects the bladder 1 to the injection port 17. However, the injection port 17 may not require the use of any insertion tube, based on the design of the particular injection port 17.

The injection port 17 must be able to allow for the injection of medications through the port while the bladder 1 is under pressure. Accordingly, the injection port 17 is a one-way valve that prevents the flow of fluids out of the injection port 17, but also allow for injection of fluids into the bladder 1. The one-way injection port 17 is a typical injection port that allows for a hypodermic needle to inject fluids through a membrane, but prevents fluids from being expelled when the needle is removed from the membrane. There a numerous suitable commercial one-way injection ports for use within the invention described herein.

FIG. 8 depicts the insertion tubing 13 and the bladder tubing 7 attached via a bladder clamp. Other suitable means exist to secure the insertion tubing 13 and bladder tubing 7 to the bladder 1 without the use of a clamp. For example, suitable adhesives or other mechanical means known in the art are suitable for securing the insertion tubing 13 and bladder tubing 7, or other feature, as required, to the bladder.

FIG. 8 further identifies a foam core 42 utilized around the bladder and within the proximal housing 2. Said foam core 42 may be injected in the proximal housing after filling the bladder 1 with fluids, or the foam core 42, may be pre-molded based on the volume of fluids to be filled.

Figure 9:
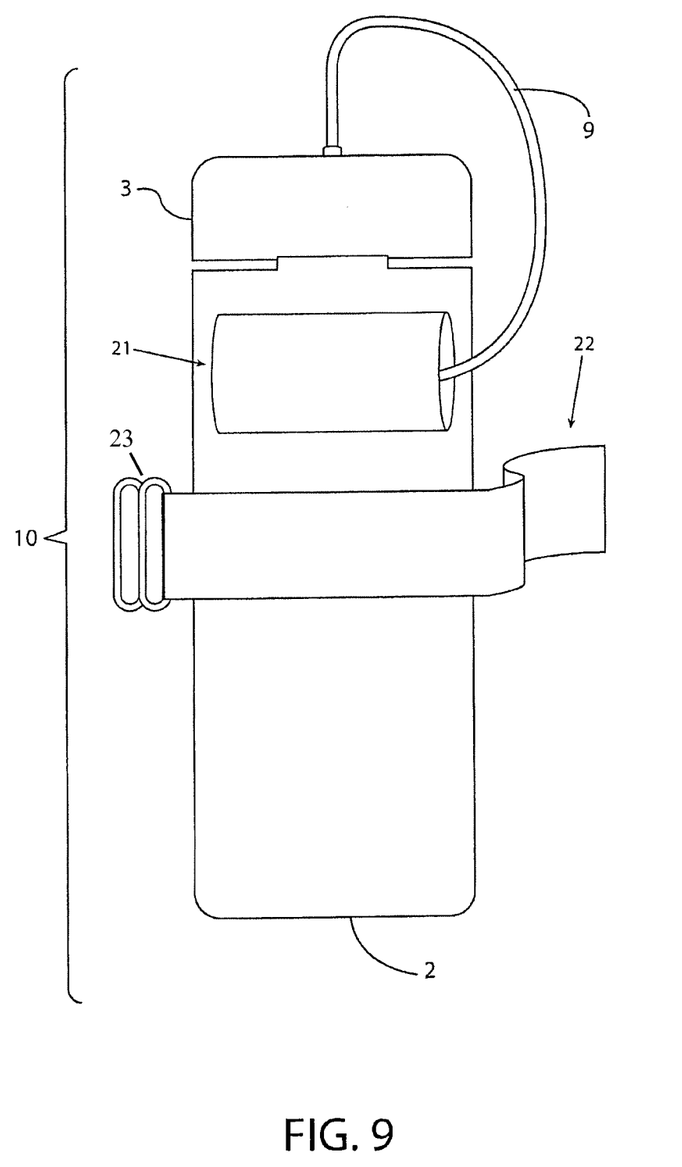
FIG. 9 is a perspective view of one embodiment of the invention described herein.

FIG. 9 depicts an embodiment of the invention described herein, that identifies the rear view of the rugged infusion device 10, with the distal housing situated at the top of the figure, and the external tubing 9 extending from the distal housing 3 into a tubing holder 21 that provides a location for the storage of tubing before or after use. Further, FIG. 9 depicts an embodiment of the invention utilizing a single strap 22 positioned around the back of the rugged infusion device 10, and a strap buckle 23 to secure the strap in place. The strap 22 may also utilize hook and loop materials, or other fastening devices. In certain other embodiments, no buckle 23 is necessary for securing the strap 22 around the rugged infusion device 10.

Figure 10:
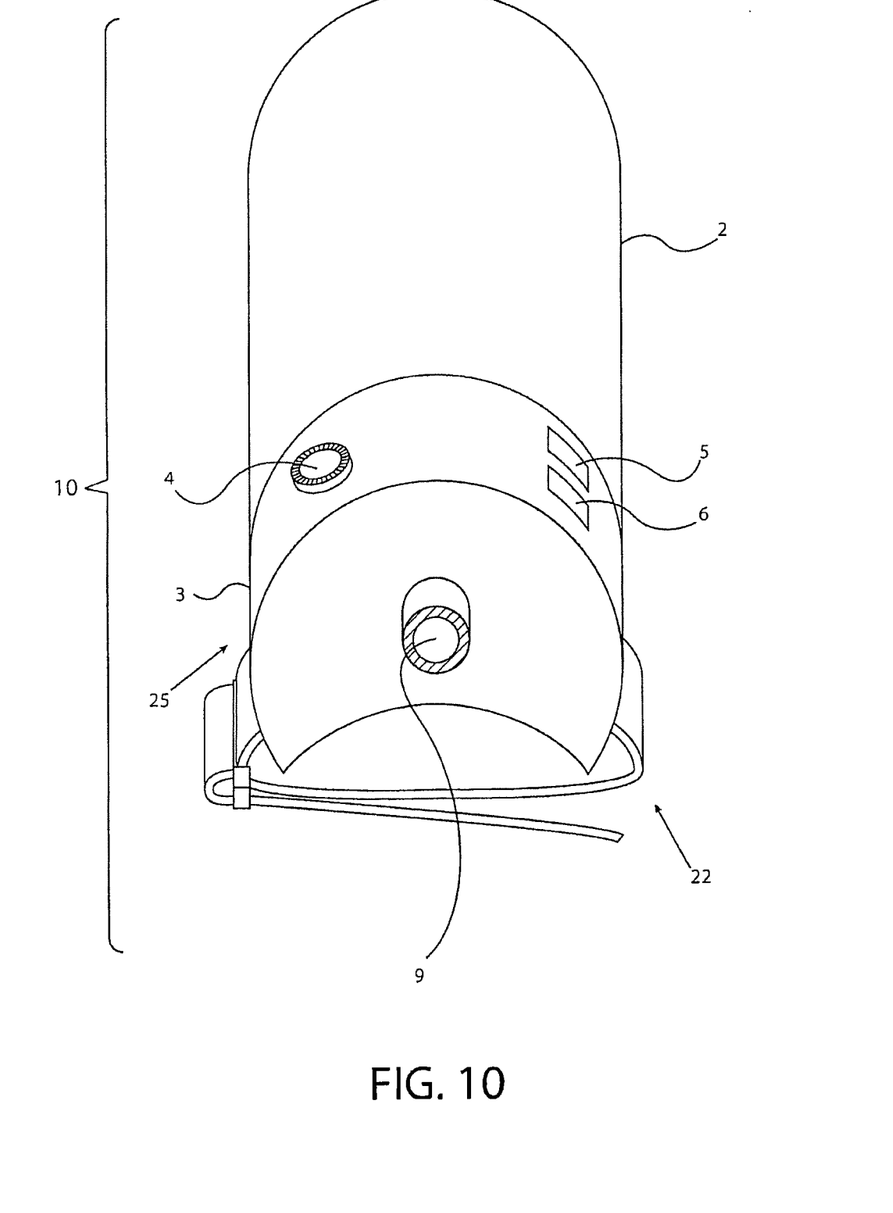
FIG. 10 is a perspective view of one embodiment of the invention described herein.

FIG. 10 identifies an embodiment of the invention described herein as viewed from the distal housing 3, where the proximal housing 2 and distal housing 3 have a concave back 25. Accordingly, in contrast to an embodiment where the proximal housing 2 is a cylinder, FIG. 10 identifies a proximal housing 2 and distal housing 3, that are partially cylindrical, but have a concave back 25, to allow a more stable attachment to a body. In particular, the invention is contemplated to be secured to an arm or a leg. Having a concave back allows a more secure attachment to an arm or leg as compared to a convex/cylindrical shaped housing. Utilizing a strap 22 that is secured only on the concave back 25 allows the strap 22 to be secured around, for example, an arm or leg, without requiring movement of a patient. The strap 22 connects to each side of the concave back 25 and does not encircle the entire upper housing 2. Thus, the rugged infusion device 10 can be placed on a body and then secured around, for example, an arm or leg, with the strap 22. This shape allows the strap to securely attach the rugged infusion device to the patient.

Figure 11:
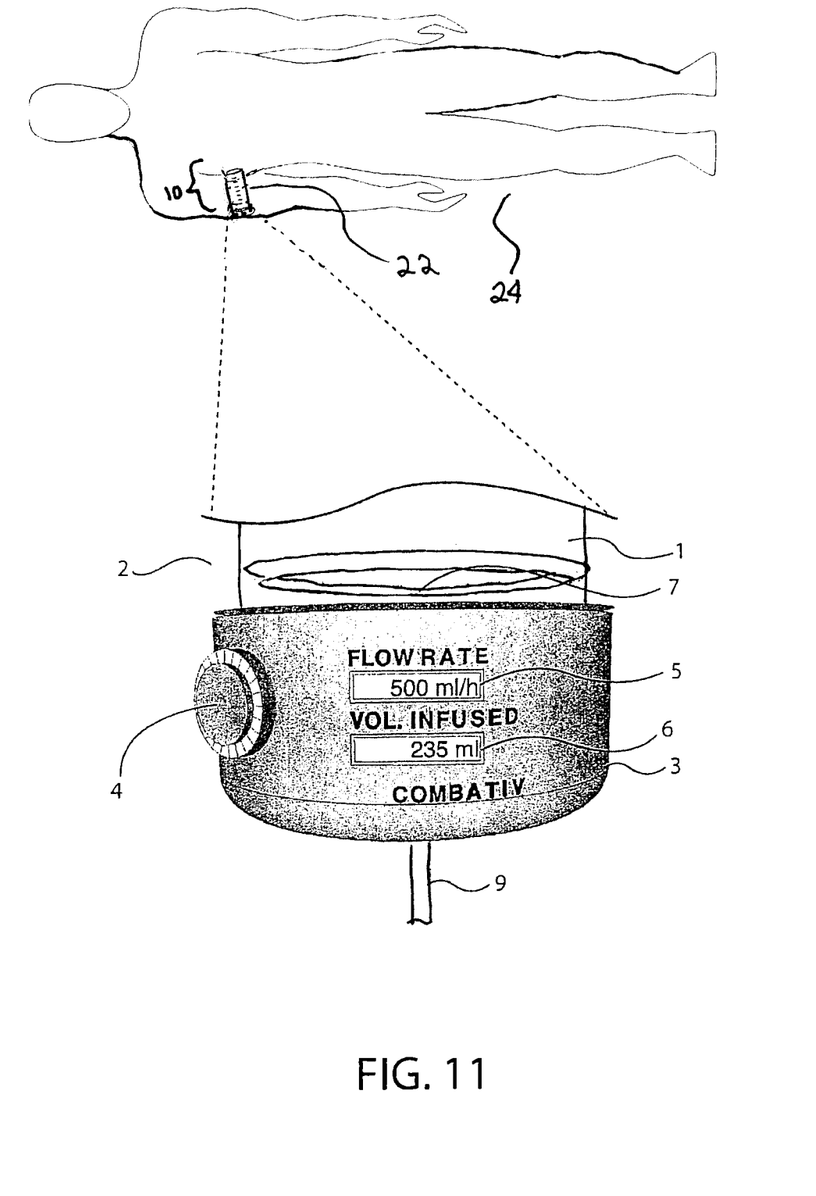
FIG. 11 is a perspective view of one embodiment of the invention described herein as attached to a patient.

FIG. 11 depicts the rugged infusion device 10 as secured to the arm of a person 24. The rugged infusion device 10 is secured to the arm via a strap 22. The ability to secure the rugged infusion device 10 to the arm of a person 24 lying down on the ground, as depicted here, provides numerous advantages over traditional IV bags which require elevation to infuse fluids. The rugged infusion device 10 is shown attached to the person 24, and then a portion of the device is shown in detail.

FIGS. 12, 13, 14, and 15 describe alternative embodiments using pressure devices other than an elastomeric bladder. Instead using other mechanical devices 100, 105, 110, or compressed air 120, to provide force to an IV bladder. These embodiments allow for the rugged device to be open to allow for the insertion of an IV bag, or in some cases pre-sealed with an IV bag for immediate use.

As described herein, the use of an alternative pressure device or a force imparting mechanism, such as the devices 100, 105, 110, or 120 may replace the elastomeric bladder and any embodiment described herein. Such devices include, but are not limited to, spring type mechanisms, screw mechanisms, lever based mechanisms, compressed air, as well as devices that utilize small electronic motors to, for example, drive the screw mechanism or impart pressure on a lever based mechanism to impart force onto the bladder.

The devices may be situated at the distal end of the rugged infusion device and provide pressure along the longitudinal axis, so to empty the bladder situated within the rugged infusion device. Alternatively, the device may be positioned along the lateral axis and impart pressure so the side of the bladder, instead of the top or bottom of the bladder as in the longitudinal orientation. Finally, the force imparting mechanism may impart forces from both the longitudinal and the lateral axes.

The invention now being fully described, it will be apparent to one of ordinary skill in the art that many changes and modifications can be made thereto without departing from the spirit or scope of the appended claims.

What is claimed is:

1. A rugged infusion device suitable for containing sterile liquids and comprising a force imparting mechanism to provide constant pressure to an IV bag and thereafter expelling said liquids; further comprising a rugged outer shell comprised of a proximal and distal parts in relation to the force imparting mechanism, and an inner proximal housing, wherein sandwiched between said outer shell and said inner proximal housing is a shock absorbing material, said distal part comprising one or more of a flow regulator and a flow meter, and wherein said rugged proximal and distal parts are capable of absorbing impacts to minimize the force imparted to the infusion device.

2. A rugged IV infusion device comprising a force imparting mechanism to provide constant pressure to an IV bag, a rugged outer shell, a flow regulator, a modulator, and a flow meter; wherein said device is capable of providing a pressure of up to 20 PSI; said rugged outer shell having a proximal and distal part in relation to said IV bag, and a rugged inner housing having a proximal and distal part in relation to the IV bag, comprising a shock absorbing material sandwiched between said outer shell and said inner housing, and wherein the proximal part of the outer shell comprises an outlet and inlet and said IV bag being contained within the proximal part; said distal part comprising the flow regulator, the modulator, and the flow meter.

3. The infusion device of claim 1 or 2 further comprising a mechanism for attaching to an IV line for effusion of fluid from the IV bag.

4. The infusion device of claim 1 or 2 further comprising straps.

5. The infusion device of claim 1 or 2 where said outer shell is made of a rigid plastic material, capable of withstanding forces of up to 300 G's.

6. The infusion device of claim 1 or 2 where said IV bag is pre-filled with a sterile fluid suitable for infusion into a mammal.

7. The infusion device of claim 1 or 2 where said flow regulator is capable of regulating the flow of fluid to about 0.1 to 100 ml per minute.

8. The infusion device of claim 1 comprising a concave side on the proximal and distal housings.

9. The infusion device of claim 1 wherein the proximal part further comprises a foam material disposed inside said inner proximal shell.

10. The infusion device of claim 1 or 2 wherein the force imparting mechanism is selected from the groups consisting of a spring mechanism, a screw mechanism, a lever mechanism, and compressed gas.

* * * * *